US00PP33104P3

(12) United States Plant Patent
Klemm et al.

(10) Patent No.: US PP33,104 P3
(45) Date of Patent: May 25, 2021

(54) ***CALIBRACHOA* PLANT NAMED 'KLECA18503'**

(50) Latin Name: ***Calibrachoa* sp.**
Varietal Denomination: KLECA18503

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/871,012

(22) Filed: May 10, 2020

(65) Prior Publication Data

US 2020/0383258 P1 Dec. 3, 2020

Related U.S. Application Data

(60) Provisional application No. 62/921,069, filed on May 29, 2019.

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 6/821; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Calibrachoa* plant designated 'KLECA18503' particularly distinguished by pink and purple bicolored flowers, is disclosed.

1 Drawing Sheet

Genus and species: *Calibrachoa* sp.
Variety denomination: 'KLECA18503'.

BACKGROUND OF THE NEW PLANT

The present invention comprises a new and distinct variety of *Calibrachoa*, botanically known as *Calibrachoa* sp., and hereinafter referred to by the variety name 'KLECA18503'. 'KLECA18503' originated from a controlled cross between the female *Calibrachoa* parent 'Hula Soft Pink', (unpatented) and the proprietary male *Calibrachoa* 'CA-2014-5086', (unpatented) in Stuttgart, Germany in August 2015.

'KLECA18503' has been found to reproduce true to type in successive generations of asexual propagation in Stuttgart, Germany via vegetative stem cuttings.

SUMMARY

The following are the most outstanding and distinguishing characteristics of 'KLECA18503' when grown under normal horticultural practices in Stuttgart, Germany.

1. Large, soft pink flowers with dark purple color at transition to corolla tube; and
2. An upright, mounding habit.

DESCRIPTION OF THE PHOTOGRAPH

This new *Calibrachoa* plant is illustrated by the accompanying photograph of a plant grown outdoors in Stuttgart, Germany. The photograph shows the whole plant, unless otherwise noted, including the flowers and foliage and buds. The colors shown are as true as can be reasonably obtained by conventional photographic procedures. The photograph is of a whole plant photo of 'KLECA18503' taken at 3-months-old in June 2018.

DESCRIPTION OF THE NEW VARIETY

The following detailed descriptions set forth the distinctive characteristics of 'KLECA18503'. The data which define these characteristics were collected from asexual reproductions carried out in Stuttgart, Germany. Data was collected on plants grown 18 weeks since potting in a greenhouse with no pinching or growth regulators. Color references are to The R.H.S. Colour Chart of The Royal Horticultural Society of London (R.H.S.), 5$^{th}$ edition (2007).

Classification:
- *Family*.—Solanaceae.
- *Botanical*.—*Calibrachoa* sp.
- *Designation*.—'KLECA18503'.

Parentage:
- *Female parent*.—'Hula Soft Pink' (unpatented).
- *Male parent*.—'CA-2014-5086' (unpatented).

Plant:
- *Life cycle*.—Annual.
- *Form*.—Short-lived subshrub.
- *Habit*.—Upright, mounding.
- *Height (from soil line to top of foliage)*.—11.0 cm.
- *Spread*.—30 cm.
- *Propagation*.—Vegetative.
- *Type cuttings*.—Tip cuttings.
- *Time to produce a rooted cutting*.—3 weeks.
- *Disease and pest resistance and susceptibility*.—To date, plants of the 'KLECA18503' have not been observed to be resistant to pathogens and pests common to *Calibrachoa* plants.

Stems:
*Stem color*.—RHS 143B.
*Pubescence*.—Present.
*Pubescence color*.—RHS 155A.
*Stem diameter*.—0.15 cm.
*Stem length*.—From soil line to first node: 1.4 cm. Total length: 25 cm.
*Internode length*.—1.2 cm.

Foliage:
*Arrangement*.—Opposite.
*Shape*.—Acute.
*Apex*.—Broadly acute.
*Base*.—Attenuate.
*Margin*.—Entire.
*Surface*.—Moderately glandular pubescent.
*Surface pubescence*.—Present.
*Pubescence color*.—RHS 155A.
*Variegation*.—Absent.
*Venation*.—Arcuate.
*Venation color*.—Upper surface: RHS 144A. Lower surface: RHS 145B.
*Length*.—4.3 cm.
*Width*.—1.6 cm.
*Color*.—Upper surface: RHS N137A. Lower surface: RHS 137B.
*Fragrance*.—Absent.

Inflorescence:
*Flowering habit*.—Single flowers.
*Flower type*.—Determinate inflorescence.
*Flowering requirements*.—A minimum of light sun is required.
*Duration of flowers*.—6 days.
*Corolla surface texture*.—Smooth.
*Shape*.—Funnel form.
*Fragrance*.—Absent.
*Lobing of the flower*.—Weak.
*Conspicuousness of the veins*.—Medium.
*Flower depth*.—2.3 cm.
*Flower tube length*.—2.1 cm.
*Flower tube diameter*.—0.7 cm.
*Flower diameter*.—4.9 cm.
*Pedicel color*.—RHS 144B.
*Pedicel length*.—2.5 cm to 4.0 cm.
*Calyx*.—Funnel shaped, salver form.

Inflorescence bud:
*Surface*.—Smooth.
*Length*.—2.7 cm.
*Diameter*.—0.6 cm.
*Shape*.—Oblong.
*Color*.—RHS 65C (limbs) and RHS 154C (throat).

Peduncles:
*Length*.—2.5 cm to 4.0 cm.
*Diameter*.—0.1 cm.
*Color*.—RHS 144B.
*Texture*.—Densely glandular pubescent.
*Anthocyanin color*.—Absent.

Sepals:
*Shape*.—Lanceolate to trullate.
*Apex*.—Narrowly acute.
*Margin*.—Entire.
*Length*.—1.9 cm.
*Diameter*.—0.5 cm.
*Sepal color*.—Upper surface: RHS 137A. Lower surface: RHS 137C.

Petals:
*Shape*.—Obcordate.
*Length*.—2.0 cm.
*Apex*.—Emarginate.
*Margin*.—Entire.
*Base*.—Fused in the tube.
*Texture, upper surface*.—Glabrous.
*Texture, lower surface*.—Glandular pubescent, dense along venation.
*Lobe length*.—2.3 cm.
*Lobe width*.—2.3 cm.
*Color*.—Lobe color: Upper surface: RHS 84C with RHS N79A at transition to corolla tube. Lower surface: RHS 84C. Corolla tube color: Inner: RHS 7A. Outer: RHS 154C.
*Fragrance*.—Absent.

Reproductive organs:
*Stamen number*.—5.
*Anther color*.—RHS 3C.
*Filament color*.—RHS 150C.
*Pollen color*.—RHS 8B.
*Pollen quantity*.—Moderate.
*Placenta arrangement*.—Ovate.
*Pistil number*.—1.
*Pistil length*.—0.7 cm.
*Stigma color*.—RHS 144C.
*Style length*.—0.8 cm.
*Style color*.—RHS 144C.

Fruit and seed set: No fruit or seed set observed.

COMPARISON OF 'KLECA18503' WITH PARENTAL LINES AND KNOWN VARIETY

'KLECA18503' is distinguished from the parental lines as follows. Whereas 'KLECA18503' has light pink flowers with a large sized dark purple transition color to the corolla tube, female parent 'Hula Soft Pink' has light pink flowers with a medium sized dark red transition color to the corolla tube and male parent 'CA-2014-5086' has light orange flowers with a medium sized red transition color to the corolla tube.

'KLECA18503' can be compared to the commercial *Calibrachoa* variety 'KLECA14263' (U.S. Plant Pat. No. 27,100), also commercially known as MINIFAMOUS Neo 'Salmon Pink+Eye' in that 'KLECA18503' flowers earlier and has larger flowers than MINIFAMOUS Neo 'Salmon Pink+Eye'.

We claim:

1. A new and distinct variety of *Calibrachoa* plant designated 'KLECA18503' as illustrated and described herein.

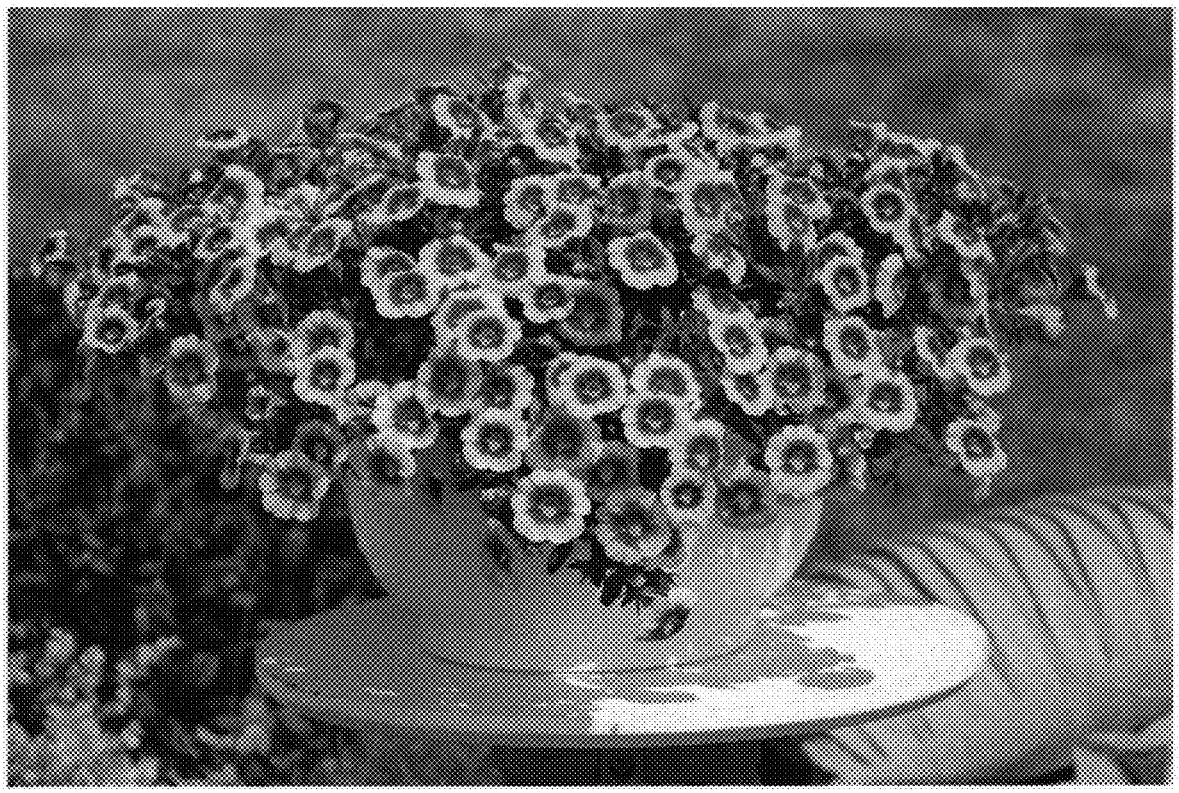

* * * * *